US012559786B2

(12) United States Patent
Zhang et al.

(10) Patent No.: US 12,559,786 B2
(45) Date of Patent: Feb. 24, 2026

(54) CRISPR/CAS AND TRANSPOSASE BASED AMPLIFICATION COMPOSITIONS, SYSTEMS AND METHODS

(71) Applicants:THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Feng Zhang, Cambridge, MA (US); Max Kellner, Cambridge, MA (US); Jonathan Gootenberg, Cambridge, MA (US); Omar Abudayyeh, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 1135 days.

(21) Appl. No.: 17/054,428

(22) PCT Filed: Jun. 26, 2019

(86) PCT No.: PCT/US2019/039195
§ 371 (c)(1),
(2) Date: Nov. 10, 2020

(87) PCT Pub. No.: WO2020/006049
PCT Pub. Date: Jan. 2, 2020

(65) Prior Publication Data
US 2021/0147915 A1      May 20, 2021

Related U.S. Application Data

(60) Provisional application No. 62/767,077, filed on Nov. 14, 2018, provisional application No. 62/690,160, filed on Jun. 26, 2018.

(51) Int. Cl.
*C12Q 1/68*          (2018.01)
*C12Q 1/6816*       (2018.01)

(52) U.S. Cl.
CPC ..... *C12Q 1/6816* (2013.01); *C12Q 2527/101* (2013.01); *C12Q 2531/113* (2013.01); *C12Y 207/07* (2013.01)

(58) Field of Classification Search
None
See application file for complete search history.

(56) References Cited

U.S. PATENT DOCUMENTS

| | | | | |
|---|---|---|---|---|
| 10,350,570 B2 * | 7/2019 | Gunderson | ............. | C12Q 1/68 |
| 10,844,372 B2 * | 11/2020 | Belhocine | .......... | C12N 15/1068 |
| 10,968,536 B2 * | 4/2021 | Brown | ................... | C40B 40/08 |
| 11,286,478 B2 * | 3/2022 | Zhang | .................. | C12N 15/63 |
| 2016/0032260 A1 | 2/2016 | Sobek et al. | | |

FOREIGN PATENT DOCUMENTS

| | | | | |
|---|---|---|---|---|
| CN | 105861552 A | 8/2016 | | |
| CN | 105950639 A | 9/2016 | | |
| JP | 2007508014 A | 4/2007 | | |
| WO | 2005/038029 A2 | 4/2005 | | |
| WO | 2014/093622 A2 | 6/2014 | | |
| WO | WO-2017015075 A1 * | 1/2017 | .......... | C12Q 1/6865 |
| WO | 2017/189308 A1 | 11/2017 | | |
| WO | 2017/219027 A1 | 12/2017 | | |
| WO | 2018/107129 A8 | 12/2017 | | |
| WO | 2018/107129 A1 | 6/2018 | | |
| WO | 2018/170340 A1 | 9/2018 | | |
| WO | 2020/006049 A1 | 1/2020 | | |

OTHER PUBLICATIONS

Gootenberg et al. (Science, 2017, 356:438-442) (Year: 2017).*
Euler et al. (J Clin Micro, 2012, 50(7):2234-2238) (Year: 2012).*
Euler et al. (J Clin Micro, 2013, 51(4):1110-1117) (Year: 2013).*
Ledoño et al. (Virol J, 2016, 13:48, 1-9) (Year: 2016).*
Daher et al. (Clin Chem 2016, 62:7, 947-958) (Year: 2016).*
Kaminski, et al., "CRISPR-based diagnostics," Nature Biomedical Engineering, vol. 5, Jul. 2021, all enclosed pages cited.
Office Action from corresponding UAE application No. P6001859/ 2020 mailed Dec. 21, 2023, all enclosed pages cited.
Search Report from corresponding UAE application No. P6001859/ 2020 mailed Dec. 21, 2023, all enclosed pages cited.
Office Action from corresponding European application No. 19739830.8 mailed Jan. 2, 2024, all enclosed pages cited.
Examination report from corresponding Canadian application No. 3,101,066 mailed Aug. 31, 2023, all enclosed pages cited.
Office Action from corresponding Chinese application No. 201980043102.2 mailed Aug. 14, 2023, all enclosed pages cited.
Search Report from corresponding Chinese application No. 201980043102.2 mailed Aug. 14, 2023, all enclosed pages cited.
Sos, et al., "Characterization of chromatin accessibility with a transposome hypersensitive sites sequencing (THS-seq) assay," Genome Biology (2016) 17:20, all enclosed pages cited.

(Continued)

*Primary Examiner* — Stephanie K Mummert
(74) *Attorney, Agent, or Firm* — F. Brent Nix, Esq.; Johnson, Marcou, Isaacs & Nix, LLC; Ming Zhang

(57)          ABSTRACT
Provided herein are methods and systems for detecting a target nucleic acid sequence. The method comprises contacting an oligonucleotide comprising the target nucleic acid sequence with a transposon complex; inserting one or more T7 RNA promoters into the oligonucleotide using the transposase; and (c) amplifying the target nucleic acid sequence. The transposon complex may comprise a transposase and a transposon sequence comprising one or more T7 RNA promoters. The target nucleic sequence may be amplified by generating RNA oligonucleotides comprising the target nucleic acid sequence via transcription from the inserted one or more T7 RNA promoters. The amplified target nucleic acid may be detected using a CRISPR Cas13-based detection system.

35 Claims, 2 Drawing Sheets

(56) References Cited

OTHER PUBLICATIONS

Chen, et al., "Single-cell whole-genome analyses by Linear Amplification via Transposon Insertion (LIANTI)," Science, 356, Apr. 14, 2017, all enclosed pages cited.

Examination report from corresponding Japanese application No. 2020-572532 mailed Jun. 13, 2023, all enclosed pages cited.

"International Preliminary Report received in Application No. PCT/US2019/039195", mailed on Jan. 7, 2021, 8 pages.

"International Search Report and Written Opinion received in Application No. PCT/US2019/039195", mailed on Oct. 10, 2019, 15 pages.

Abudayyeh, et al., "C2C2 is a Single-Component Programmable RNA-Guided RNA-Targeting CRISPR Effector", Science, vol. 353, No. 6299, Aug. 5, 2016, 23 pages.

Buenrostro, et al., "Transposition of Native Chromatin for Fast and Sensitive Epigenomic Profiling of Open Chromatin, DNA-Binding Proteins and Nucleosome Position", Nature Methods, vol. 10, No. 12, Oct. 6, 2013, 1213-1218.

Carr, et al., "Genome Engineering", Nature Biotechnology, vol. 27, No. 12, Dec. 9, 2009, 1151-1162.

Du, et al., "Coupling Sensitive Nucleic Acid Amplification with Commercial Pregnancy Test Strips", Angewandte Chemie International Edition in English, vol. 56, No. 4, Jan. 19, 2017, 12 pages.

East-Seletsky, et al., "Two Distinct RNase Activities of CRISPR-C2c2 Enable Guide-RNA Processing and RNA Detection", Nature, vol. 538, No. 7624, Oct. 13, 2016, 17 pages.

Gaudelli, et al., "Programmable Base Editing of A•T to G•C in Genomic DNA without DNA Cleavage", Nature, vol. 551, No. 7681, Nov. 23, 2017, 37 pages.

Gootenberg, et al., "Multiplexed and Portable Nucleic Acid Detection Platform with Cas13, Cas12a, and Csm6", Science, vol. 360, No. 6387, Apr. 27, 2018, 14 pages.

Gootenberg, et al., "Nucleic Acid Detection with CRISPR-Cas13a/C2c2", Science, vol. 356, No. 6336, Apr. 28, 2017, 6 pages.

Goryshin, et al., "Insertional Transposon Mutagenesis by Electroporation of Released Tn5 Transposition Complexes", Nature Biotechnology, vol. 18, Jan. 2000, 97-100.

Green, et al., "Toehold Switches: De-Novo-Designed Regulators of Gene Expression", Cell, vol. 159, No. 4, Nov. 6, 2014, 28 pages.

Gruber, et al., "The Vienna RNA Websuite", Nucleic Acids Research, vol. 36, Apr. 19, 2008, W70-W74.

Komor, et al., "Programmable Editing of a Target Base in Genomic DNA without Double-Stranded DNA Cleavage", Nature, vol. 533, No. 7603, May 19, 2016, 17 pages.

Kumar, et al., "Deconstructing Transcriptional Heterogeneity in Pluripotent Stem Cells", Nature. vol. 516, Dec. 4, 2014, 56-61.

Lei, et al., "Repurposing CRISPR as an RNA-Guided Platform for Sequence-Specific Control of Gene Expression", Cell, vol. 152, No. 5, Feb. 28, 2013, 1173-1183.

Myhrvold, et al., "Field-Deployable Viral Diagnostics Using CRISPR-Cas13", Science, vol. 360, Apr. 27, 2018, 444-448.

Nakamura, et al., "Codon Usage Tabulated from the International DNA Sequence Databases: Status For the Year 2000", Nucleic Acids Research, vol. 28, No. 1, Jan. 1, 2000, 292 page.

Nishida, et al., "Targeted Nucleotide Editing Using Hybrid Prokaryotic and Vertebrate Adaptive Immune Systems", Science, vol. 353, Issue 6305, Aug. 4, 2016, 35 pages.

Pardee, et al., "Paper-Based Synthetic Gene Networks", Cell, vol. 159, No. 4, Nov. 6, 2014, 28 pages.

Pardee, et al., "Rapid, Low-Cost Detection of Zika Virus Using Programmable Biomolecular Components", Cell, vol. 165, No. 5, May 19, 2016, 24 pages.

Shmakov, et al., "Discovery and Functional Characterization of Diverse Class 2 CRISPR-Cas Systems", Molecular Cell, vol. 60, No. 3, Nov. 5, 2015, 385-397.

Smargon, et al., "Cas 13B is a Type VI-B CRISPR-Associated RNA-Guided RNAse Differentially Regulated by Accessory Proteins Csx27 and Csx28", Molecular Cell, vol. 65, No. 4, Feb. 16, 2017, 30 pages.

Strecker, et al., "RNA-Guided DNA Insertion with CRISPR-associated Transposases", Science, vol. 365, No. 6448, Sep. 5, 2019, 48-53.

Urdea, et al., "Requirements for High Impact Diagnostics in the Developing World", Nature, vol. 444, 2006, 73-79.

York, et al., "Simple and Efficient Generation in Vitro of Nested Deletions and Inversions: Tn5 Intramolecular Transposition", Nucleic Acids Research, vol. 26, No. 8, 1998, 1927-1933.

Zuker, et al., "Optimal Computer Folding of Large RNA Sequences Using Thermodynamics and Auxiliary Information", Nucleic Acids Research, vol. 9, No. 1, 1981, 133-148.

Gootenberg, et al., Supplementary Materials for "Multiplexed and portable nucleic acid detectio platform with Cas13, Cas12a, and Csm6," Science, Feb. 15, 2018, all enclosed pages cited.

Examination report from corresponding European application No. 19739830.8 mailed Apr. 3, 2023, all enclosed pages cited.

Office Action from corresponding Saudi Arabian application No. 520420790 mailed Mar. 29, 2022, all enclosed pages cited.

Li, et al., "The successes and future prospects of the linear antisense RNA amplification methodology," Nature Protocols, vol. 13, No. 5, all enclosed pages cited, 2018.

Li, et al., "CRISPR-Cas12a-assisted nucleic acid detection," Cell Discovery (2018), 4:20, all enclosed pages cited.

Office Action from corresponding Saudi Arabian application No. 520420790 mailed Dec. 26, 2022, all enclosed pages cited.

Office Action from corresponding Israeli application No. 278751 mailed Sep. 26, 2024, all enclosed pages cited.

* cited by examiner

CRISPR/CAS AND TRANSPOSASE BASED AMPLIFICATION COMPOSITIONS, SYSTEMS AND METHODS

CROSS-REFERENCE TO RELATED APPLICATIONS

This application is a national phase entry of International Application No. PCT/US2019/039195 filed Jun. 26, 2019, which claims the benefit of U.S. Provisional Applications No. 62/690,160, filed Jun. 26, 2018 and U.S. Provisional Application No. 62/767,077, filed Nov. 14, 2018. The entire contents of the above-identified applications are hereby fully incorporated herein by reference.

STATEMENT REGARDING FEDERALLY SPONSORED RESEARCH

This invention was made with government support under Grant Nos. MH100706, MH110049, and HL141201 awarded by the National Institutes of Health. The government has certain rights in the invention.

TECHNICAL FIELD

The subject matter disclosed herein is generally directed to nucleic acid amplification methods, systems, and rapid diagnostics related to the use of CRISPR effector systems.

BACKGROUND

Nucleic acids are a universal signature of biological information. The ability to rapidly detect nucleic acids with high sensitivity and single-base specificity on a portable platform has the potential to revolutionize diagnosis and monitoring for many diseases, provide valuable epidemiological information, and serve as a generalizable scientific tool. Although many methods have been developed for detecting nucleic acids (Du et al., 2017; Green et al., 2014; Kumar et al., 2014; Pardee et al., 2014; Pardee et al., 2016; Urdea et al., 2006), they inevitably suffer from trade-offs among sensitivity, specificity, simplicity, and speed. For example, qPCR approaches are sensitive but are expensive and rely on complex instrumentation, limiting usability to highly trained operators in laboratory settings. As nucleic acid diagnostics become increasingly relevant for a variety of healthcare applications, detection technologies that provide high specificity and sensitivity at low cost would be of great utility in both clinical and basic research settings.

Many nucleic acid amplification approaches are available with various detection platforms. Among them, isothermal nucleic acid amplification methods have been developed for amplification without drastic temperature cycling and complex instrumentations. These methods include nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). These isothermal amplification approaches, however, may still require an initial denaturation step and multiple sets of primers. Furthermore, novel approaches combining isothermal nucleic acid amplification with portable platforms (Du et al., 2017; Pardee et al., 2016), offer high detection specificity in a point-of-care (POC) setting, but have somewhat limited applications due to low sensitivity.

SUMMARY

In one aspect, the invention provides a method of detecting a target nucleic acid sequence. The method comprises (a) contacting an oligonucleotide comprising the target nucleic acid sequence with a transposon complex; (b) inserting one or more RNA polymerase promoters into the oligonucleotide using the transposase; and (c) amplifying the target nucleic acid sequence. The transposon complex may comprise a transposase and a transposon sequence comprising one or more RNA polymerase promoters. The target nucleic sequence may be amplified by generating RNA oligonucleotides comprising the target nucleic acid sequence via transcription from the inserted one or more RNA polymerase promoters.

In some embodiments, the method may further comprise detecting the amplified target nucleic acid. The amplified target nucleic acid may be detected using a CRISPR Cas13-based detection system. In alternative embodiments, the target nucleic acid may be detected using a CRISPR Cas12-based detection system.

In some embodiments, the transposase may be a Tn5 transposase, a Mu transposase, a Tn7 transposase, or engineered transposase. The Tn5 transposase may comprise two 19 base pair Mosaic End (ME) Tn5 transposase recognition sequences. The engineered transposase may be optimized to function at between 30° C. and 45° C. The engineered transposase may be optimized to function at between 35° C. and 40° C. The engineered transposase may be optimized to release from the oligonucleotide at a faster rate compared to a wild type transposase.

Insertion of the one or more T7 RNA promoters into the double-stranded polynucleotide may be random, or it may occur in a GC rich region.

The CRISPR Cas13-based detection system may comprise a Cas13 enzyme that is from an organism of a genus selected from the group consisting of: *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter,* and *Lachnospira.*

The CRISPR Cas13-based detection system may comprise a Cas13 enzyme that is from the group consisting of: *Leptotrichia shahii; Leptotrichia wadei* (Lw2)*; Listeria seeligeri; Lachnospiraceae bacterium* MA2020*; Lachnospiraceae bacterium* NK4A179; [*Clostridium*] *aminophilum* DSM 10710*; Carnobacterium gallinarum* DSM 4847*; Carnobacterium gallinarum* DSM 4847 (second CRISPR Loci)*; Paludibacter propionicigenes* WB4*; Listeria weihenstephanensis* FSL R9-0317*; Listeriaceae bacterium* FSL M6-0635*; Leptotrichia wadei* F0279*; Rhodobacter capsulatus* SB 1003*; Rhodobacter capsulatus* R121*; Rhodobacter capsulatus* DE442*; Leptotrichia buccalis* C-1013-b*; Herbinix hemicellulosilytica;* [*Eubacterium*] *rectale; Eubacteriaceae bacterium* CHKCI004*; Blautia* sp. *Marseille*-P2398*; Leptotrichia* sp. oral taxon 879 str. F0557*; Lachnospiraceae bacterium* NK4A144*; Chloroflexus aggregans; Demequina aurantiaca; Thalassospira* sp. TSL5-1*; Pseudobutyrivibrio* sp. OR37*; Butyrivibrio* sp. YAB3001*; Blautia* sp. Marseille-P2398*; Leptotrichia* sp. Marseille-P3007; *Bacteroides ihuae; Porphyromonadaceae bacterium* KH3CP3RA*; Listeria riparia;* and *Insolitispirillum peregrinum.*

The CRISPR Cas12-based detection system may comprise a Cas12a or Cas12b enzyme. The Cas12-based detection system may comprise a Cas12 enzyme that is from an organism of a genus selected from the group consisting of *Francisella tularensis, Prevotella albensis, Lachnospiraceae bacterium, Butyrivibrio proteoclasticus, Peregrinibacteria bacterium, Parcubacteria bacterium, Smithella* sp., *Acidaminococcus* sp., *Lachnospiraceae bacterium, Candidatus Methanoplasma termitum, Eubacterium eligens, Moraxella bovoculi, Leptospira inadai, Porphyromonas crevioricanis, Prevotella disiens* and *Porphyromonas macacae, Succinivibrio dextrinosolvens, Prevotella disiens, Flavobacterium branchiophilum, Helcococcus kunzii, Eubacterium* sp., *Microgenomates (Roizmanbacteria) bacterium, Flavobacterium* sp., *Prevotella brevis, Moraxella caprae, Bacteroidetes oral, Porphyromonas cansulci, Synergistes jonesii, Prevotella bryantii, Anaerovibrio* sp., *Butyrivibrio fibrisolvens, Candidatus methanomethylophilus, Butyrivibrio* sp., *Oribacterium* sp., *Pseudobutyrivibrio ruminis* and *Proteocatella sphenisci.*

In certain embodiments, the method may not require heating the oligonucleotide.

In certain embodiments, amplification of the target nucleic acid sequence may be performed at a constant temperature.

In some embodiments, the target nucleic acid sequence may be about 20-30, about 30-40, about 40-50, or about 50-100 nucleotides in length. The target nucleic acid sequence may be about 100-200, about 100-500, or about 100-1000 nucleotides in length. The target nucleic acid sequence may be about 1000-2000, about 2000-3000, about 3000-4000, or about 4000-5000 nucleotides in length.

In some embodiments, the method may further comprise detecting the amplified nucleic acid by a method selected from the group consisting of gel electrophoresis, intercalating dye detection, PCR, real-time PCR, fluorescence, Fluorescence Resonance Energy Transfer (FRET), mass spectrometry, real-time RPA, real-time LAMP, real-time NEAR, real-time HDA, real-time TMA, real-time NASBA, and CRISPR/Cas-based detection methods.

The method may allow for detection of the target nucleic acid at femtomolar sensitivity. The method may allow for detection of the target nucleic acid at attomolar sensitivity.

The target nucleic acid may be genomic DNA, mitochondrial DNA, viral DNA, plasmid DNA, or synthetic double-stranded DNA.

The oligonucleotide comprising the target nucleic acid may be an RNA oligonucleotide, and the method may comprise a reverse transcription step prior to contacting the oligonucleotide with the transposon complex.

In some embodiments, the sample may be a biological sample or an environmental sample. The biological sample may be a blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate sample, or fluid obtained from a joint, or a swab of skin or mucosal membrane surface. In specific embodiments, the sample is blood, plasma or serum obtained from a human patient.

In some embodiments, the sample may be a plant sample. In some embodiments, the sample may be a crude sample. In some embodiments, the sample may be a purified sample.

In another aspect, the invention provides a system for detecting a target nucleic acid sequence in a sample. The system may comprise a transposon complex, a T7 RNA polymerase, and a CRISPR Cas13-based detection system for detecting the transcribed target nucleic acid. In alternative embodiments, the detection system may be a CRISPR Cas12-based detection system.

In some embodiments, the transposon complex may comprise a transposase and a transposon sequence comprising one or more T7 RNA promoters. The transposase may insert the one or more T7 RNA promoters into a double-stranded polynucleotide comprising the target nucleic acid sequence.

In some embodiments, the T7 polymerase may transcribe the target nucleic acid from the inserted one or more T7 promoters.

In specific embodiments, the transposase may be a Tn5 transposase or variant thereof. In some embodiments, the transposon sequence may comprise two 19 base pair ME Tn5 transposase recognition sequences.

In specific embodiments, the CRISPR Cas13-based detection system may be a Cas13-based detection system.

In some embodiments, the system for detecting a target nucleic acid sequence may further comprise nucleic acid amplification reagents. In some embodiments, the system may further comprise reagents for performing reverse transcription.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which.

Figure 1:
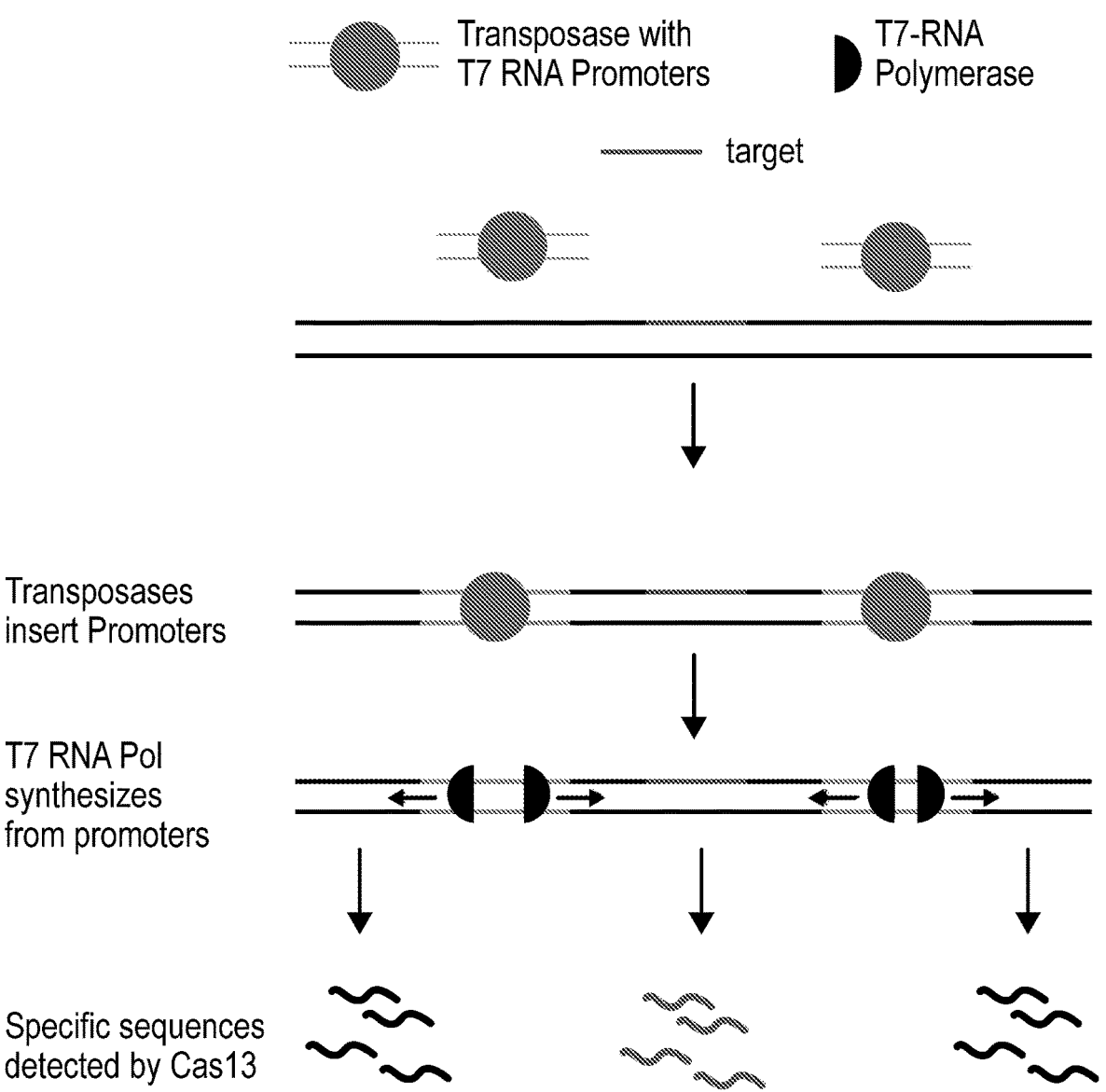
FIG. 1 is a schematic illustrating an example CRISPR/Cas-transposase amplification workflow.
Figure 2:
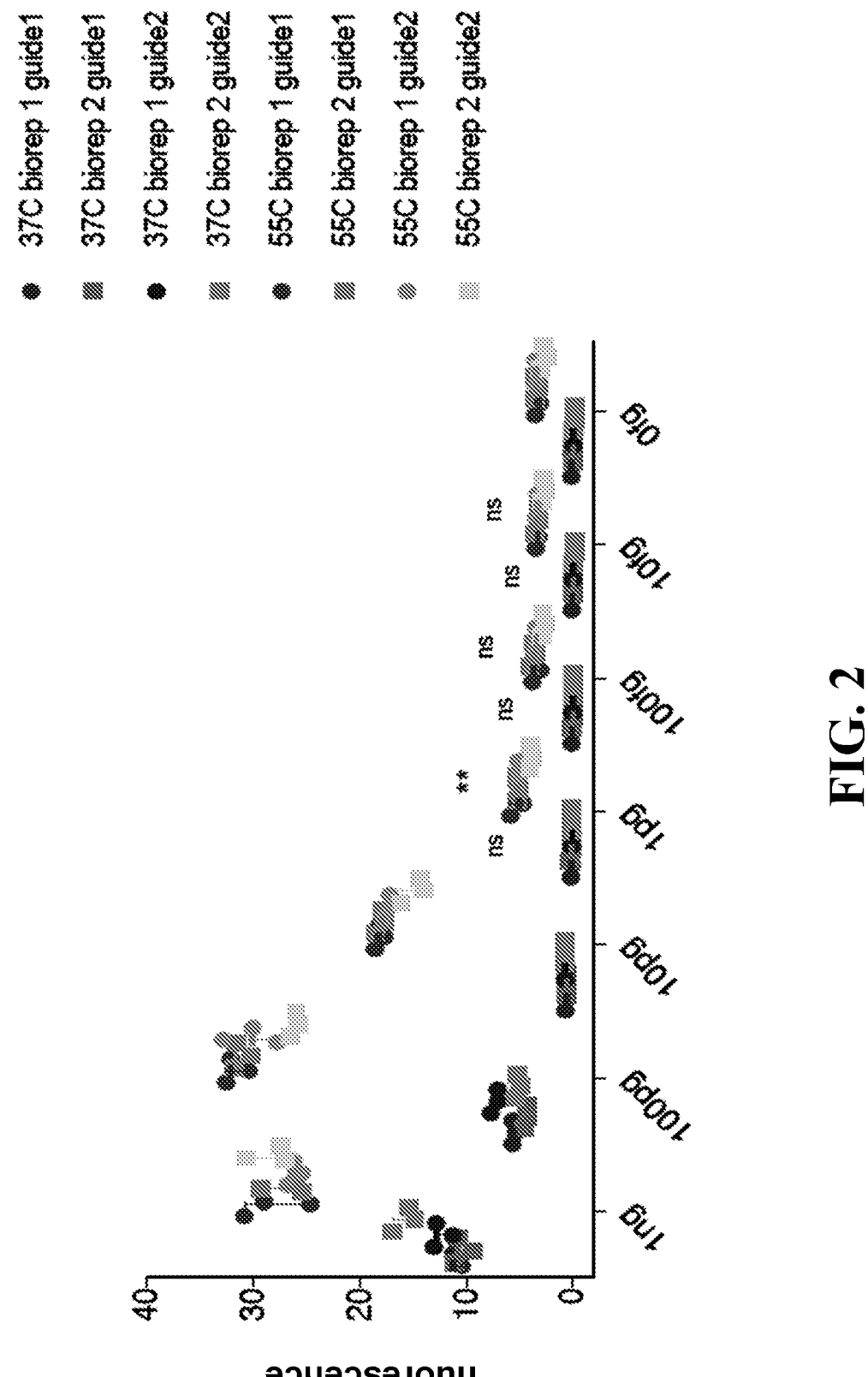
FIG. 2 is a graph showing detection of amplified target sequences at various concentrations and temperatures.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "some embodiments", "an embodiment," "an example embodiment," means that a particular feature, structure or characteristic described in connection with the embodiment is included in at least one embodiment of the present invention. Thus, appearances of the phrases "in some embodiments," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "melting", "unwinding" or "denaturing" refer to separating all or part of two complementary strands of a nucleic acid duplex.

"Nuclease" and "endonuclease" are used interchangeably herein to mean an enzyme which possesses endonucleolytic catalytic activity for DNA cleavage.

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22 (4): 359-66. doi: 10.1002/pro.2225.). See also Shmakov et al. (2015) for application in the field of CRISPR-Cas loci. Homologous proteins may but need not be structurally related, or are only partially structurally related.

"C2c2" is now referred to as "Cas13a", and the terms are used interchangeably herein unless indicated otherwise. The terms "Group 29," "Group 30," and Cas13b are used interchangeably herein. The terms "Cpf1" and "Cas12a" are used interchangeably herein. The terms "C2c1" and "Cas12b" are used interchangeably herein.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide systems and methods for isothermal amplification of target nucleic acid sequences by contacting oligonucleotides containing the target nucleic acid sequence with a transposon complex. The oligonucleotides may be single stranded or double stranded RNA, DNA, or RNA/DNA hybrid oligonucleotides. The transposon complex comprises a transposase and a transposon sequence comprising one or more RNA polymerase promoters. The transposase facilitates insertion of the one or more RNA polymerase promoters into the oligonucleotide. A RNA polymerase promoter can then transcribe the target nucleic acid sequence from the inserted one or more RNA polymerase promoters. One advantage of this system is that there is no need to heat or melt double-stranded DNA templates, since RNA polymerase polymerases require a double-stranded template. Such isothermal amplification is fast and simple, obviating the need for complicated and expensive instrumentation for denaturation and cooling. In certain example embodiment the RNA polymerase promoter is a native of modified T7 RNA promoter.

Methods of Detecting Target Nucleic Acid Sequences

In certain example embodiments, the invention provides a method of detecting a target nucleic acid sequence, comprising: (a) contacting an oligonucleotide comprising the target nucleic acid sequence with a transposon complex, wherein the transposon complex comprises a transposase and a transposon sequence comprising one or more RNA polymerase promoters; (b) inserting the one or more T7 RNA promoters into the oligonucleotide using the transposase; and (c) amplifying the target nucleic acid sequence by generating RNA oligonucleotides comprising the target nucleic acid sequence via transcription from the inserted one or more T7 RNA promoters.

Methods provided herein may comprise contacting an oligonucleotide comprising the target nucleic acid sequence with a transposon complex. The term "oligonucleotide" as used herein may refer to, but is not necessarily limited to, nucleic acid polymers that are designed to hybridize specifically to DNA or RNA sequences. The term "contacting" as described herein refers to placement in direct physical association, including both in solid or liquid form. The term "transposon", as used herein, refers to a nucleic acid segment, which is recognized by a transposase or an integrase enzyme and which is an essential component of a functional nucleic acid-protein complex (i.e. a transposome) capable of transposition. The term "transposase" as used herein refers to an enzyme, which is a component of a functional nucleic acid-protein complex capable of transposition and which is mediating transposition. The term "transposase" also refers to integrases from retrotransposons or of retroviral origin. Transposon complexes form between a transposase enzyme and a fragment of double stranded DNA that contains a specific binding sequence for the enzyme, termed "transposon end". The sequence of the transposon binding site can be modified with other bases, at certain positions, without affecting the ability for transposon complex to form a stable structure that can efficiently transpose into target DNA.

The term "target nucleic acid sequence" or "target DNA or RNA" or "target nucleic acid" refers to a DNA or RNA polynucleotide being or comprising the target sequence. In other words, the target DNA or RNA may be a DNA or RNA polynucleotide or a part of a DNA or RNA polynucleotide to which a part of the gRNA, i.e. a guide sequence, is designed to have complementarity and to which the effector function mediated by the complex comprising CRISPR effector protein and a gRNA is to be directed. In some embodiments, the target sequence is located in the nucleus or cytoplasm of a cell. In some embodiments, the oligonucleotide may be double-stranded. In some embodiments, insertions of the T7 RNA polymerase promoters into the double-stranded oligonucleotide occurs in a GC rich region of the double-stranded oligonucleotide.

In some embodiments, the target nucleic acid sequence may come from a sample. In certain embodiments, the sample may include, but is not necessarily limited to, a biological sample or an environmental sample. The biological sample may include, but is not necessarily limited to, blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate, or fluid obtained from a joint, or a swab of skin or mucosal membrane surface. In specific embodiments, the sample may be blood, plasma or serum obtained from a human patient. In some embodiments, the sample may be a plant sample. In some embodiments, the sample may be a crude sample. In some embodiments, the sample may be a purified sample.

In some embodiments, the oligonucleotide comprising the target nucleic acid may be genomic DNA, mitochondrial DNA, viral DNA, plasmid DNA, or synthetic double-stranded DNA. In some embodiments, the oligonucleotide comprising the target nucleic acid may be an RNA oligonucleotide, and the method may comprise a reverse transcription step prior to contacting the oligonucleotide with the transposon complex.

In embodiments provided herein, the transposon complex may comprise a transposase and a transposon sequence comprising one or more RNA polymerase promoters. The term "promoter" refers to a region of DNA involved in binding the RNA polymerase to initiate transcription. In specific embodiments, the RNA polymerase promoter may be a T7 RNA polymerase promoter. The T7 RNA promoter may be inserted into the double-stranded polynucleotide using the transposase. In some embodiments, insertion of the T7 RNA polymerase promoter into the oligonucleotide may be random.

The frequency of transposition is very low for most transposons, which use complex mechanisms to limit activity. Tn5 transposase, for example, utilizes a DNA binding sequence that is suboptimal and the C-terminus of the transposase interferes with DNA binding. Mechanisms involved in Tn5 transposition have been carefully characterized by Reznikoff and colleagues. Tn5 transposes by a cut-and-paste mechanism. The transposon has two pairs of 19 bp elements that are utilized by the transposase: outside elements (OE) and inside elements (IE). One transposase monomer binds to each of the two elements that are utilized. After a monomer is bound to each end of the transposon, the two monomers dimerize, forming a synapse. Vectors with donor backbones of at least 200 bp, but less than 1000 bp, are most functional for transposition in bacteria. Transposon cleavage occurs by trans catalysis and only when monomers bound to each DNA end are in a synaptic complex. Tn5 transposes with a relaxed target site selection and can therefore insert into target DNA with little to no target sequence specificity.

The natural downregulation of Tn5 transposition can be overcome by selection of a hyperactive transposase and by optimizing the transposase-binding elements [York et al. 1998]. A mosaic element (ME), made by modification of three bases of the wild type OE, led to a 50-fold increase in transposition events in bacteria as well as cell-free systems. The combined effect of the optimized ME and hyperactive mutant transposase is estimated to result in a 100-fold increase in transposition activity. Goryshin et al showed that preformed Tn5 transposition complexes could be functionally introduced into bacterial or yeast by electroporation [Goryshin et al. 2000]. Linearization of the DNA, to have inverted repeats precisely positioned at both ends of the transposon, allowed Goryshin and coworkers to bypass the cutting step of transposition thus enhancing transposition efficiency.

In some embodiments, the transposase may be used to tagment the oligonucleotide sequence comprising the target sequence. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In some embodiments, the transposase may be a Tn5 transposase. In some embodiments, the transposase may be a variant of a Tn5 transposase, or an engineered transposase. Transposases may be engineered using any method known in the art. The engineered transposase may be optimized to function at a temperature ranging from 30° C. to 45° C., 35° C. to 40° C. or any temperature in between. The engineered transposase may be optimized to release from the oligonucleotide at a faster rate compared to a wild type transposase.

In some embodiments, the transposase may be a Tn5 transposase, a Mu transposase, or a Tn7 transposase. Transposition efficiency in vitro may vary depending on the transposon system used. Generally, Tn5 and Mu transposases effect higher levels of transposition efficiency. In some embodiments, insertion may be random. In some embodiments, insertion may occur in GC rich regions of the target sequence.

In some embodiments, the transposon sequence may comprise two 19 base pair Mosaic End (ME) Tn5 transposase recognition sequences. Tn5 transposases will generally transpose any DNA sequence contained between such short 19 base pair ME Tn5 transposase recognition sequences.

In some embodiments, use of at transposase allows for separation of a double-stranded polynucleotide in the absence of heat or melting.

Amplification

In certain example embodiments, the invention provides methods for amplifying a target nucleic acid sequence. As described elsewhere herein, the term "target nucleic acid sequence" or "target DNA or RNA" or "target nucleic acid" refers to a DNA or RNA polynucleotide being or comprising the target sequence. In other words, the target DNA or RNA may be a DNA or RNA polynucleotide or a part of a DNA or RNA polynucleotide to which a part of the gRNA, i.e. a guide sequence, is designed to have complementarity and to which the effector function mediated by the complex comprising CRISPR effector protein and a gRNA is to be directed. In some embodiments, a target sequence is located in the nucleus or cytoplasm of a cell.

In embodiments provided herein, methods of detecting target nucleic acid sequences may further comprise transcribing the target nucleic acid sequence using any inserted T7 RNA promoters. The target nucleic acid sequence may be amplified by generating RNA oligonucleotides comprising the target nucleic acid sequence.

One embodiment of the invention may comprise amplifying the target nucleic acid sequence. The amplification can be isothermal and selected for temperature. In one embodiment, the amplification proceeds rapidly at 37 degrees. In other embodiments, the temperature of the isothermal amplification may be chosen by selecting a polymerase operable at a different temperature. The polymerase can be selected from the group consisting of Bst 2.0 DNA polymerase, Bst 2.0 WarmStart DNA polymerase, Bst 3.0 DNA polymerase, full length Bst DNA polymerase, large fragment Bst DNA polymerase, large fragment Bsu DNA polymerase, phi29 DNA polymerase, T7 DNA polymerase, and Sequenase DNA polymerase. In specific embodiments, amplification of the target nucleic acid sequence is performed at a constant temperature.

The amplification can be used to amplify target nucleic acid sequences with varying lengths. For example, the target nucleic acid sequence can be about 10-20, about 20-30, about 30-40, about 40-50, about 50-100, about 100-200, about 100-500, about 100-1000, about 1000-2000, about 2000-3000, about 3000-4000, or about 4000-5000 nucleotides in length. The target nucleic acid can be DNA, for example, genomic DNA, mitochondrial DNA, viral DNA, plasmid DNA, or synthetic double-stranded DNA. The target nucleic acid can be single-stranded nucleic acid, for example, an RNA molecule. The single-stranded nucleic acid can be converted to a double-stranded nucleic acid prior to based amplification. For example, an RNA molecule can be converted to a double-stranded DNA by reverse transcription prior to amplification. The single-stranded nucleic acid can be selected from the group consisting of single-stranded viral DNA, viral RNA, messenger RNA, ribosomal RNA, transfer RNA, microRNA, short interfering RNA, small nuclear RNA, synthetic RNA, and synthetic single-stranded DNA.

The isothermal amplification method can be combined with a variety of detection methods to detect the amplified nucleic acid products. For example, the detection methods can comprise gel electrophoresis, intercalating dye detection, PCR, real-time PCR, fluorescence, Fluorescence Resonance Energy Transfer (FRET), mass spectrometry, real-time RPA, real-time LAMP, real-time NEAR, real-time HDA, real-time transcription-mediated amplification (TMA), real-time NASBA, and CRISPR-SHERLOCK. The combined amplification and detection can achieve attomolar sensitivity or femtomolar sensitivity.

The amplification method can include, but is not necessarily limited to, nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR).

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride (MgCl$_2$), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [(NH$_4$)$_2$SO$_4$], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

In certain embodiments, detection of DNA with the methods or systems of the invention requires transcription of the (amplified) DNA into RNA prior to detection.

In certain embodiments, target nucleic acid sequences may be amplified by generating RNA oligonucleotides comprising the target nucleic acid sequence via transcription from the inserted one or more T7 RNA promoters.

In certain embodiments, target nucleic acid sequences may comprise RNA. In such instances, the method may comprise reverse transcribing the target sequence prior to contacting the target oligonucleotide with a transposon complex.

It will be evident that detection methods of the invention can involve nucleic acid amplification and detection procedures in various combinations. The nucleic acid to be detected can be any naturally occurring or synthetic nucleic acid, including but not limited to DNA and RNA, which may be amplified by any suitable method to provide an intermediate product that can be detected. Detection of the intermediate product can be by any suitable method including but not limited to binding and activation of a CRISPR protein which produces a detectable signal moiety by direct or collateral activity.

Detection

In certain example embodiments, the amplified target nucleic acid may be further detected using a detection method. Detecting the amplified nucleic acid may comprise detection using intercalating dyes, PCT, real-time PCR, fluorescent probes, FRET, or mass spectroscopy. In certain example embodiments, the amplified target nucleic acid sequence may be detected by a CRISPR-Cas based detection system. In certain example embodiments, the CRISPR-Cas based detection system may comprise a CRISPR Cas13-based detection system. Example CRISPR-Cas13 based detection systems are described in Gootenberg et al. Science 360, 439-444 (2018) and International Patent Application No. WO/2018/107129 which are incorporated herein by reference. Example CRISPR-Cas13 based detection systems are also described in International Patent Application No. WO 2018/170340, which is incorporated herein by reference in its entirety, with particular emphasis on paragraphs to [0261].

CRISPR Systems

In general, a Microbial Clustered Regularly Interspaced Short Palindromic Repeats (CRISPR) or CRISPR-associated (CRISPR-Cas) or system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). When the CRISPR protein is a Cpf1 protein, a tracrRNA is not required.

Embodiments provided herein utilize RNA targeting effectors to provide a robust CRISPR-based detection method with attomolar sensitivity. Embodiments disclosed herein can detect RNA with comparable levels of sensitivity and can differentiate targets from non-targets based on single base pair differences. For ease of reference, the embodiments disclosed herein may also be referred to as SHER-LOCK (Specific High-sensitivity Enzymatic Reporter unLOCKing).

Embodiments described herein provide for detection of transcribed target nucleic acid using a CRISPR-SHER-LOCK method.

Although both Cas9 and Cpf1 target DNA, single effector RNA-guided RNases have been recently discovered (Shmakov et al., 2015) and characterized (Abudayyeh et al., 2016; Smargon et al., 2017), including C2c2, providing a platform for specific RNA sensing. RNA-guided RNases can be easily and conveniently reprogrammed using CRISPR RNA (crRNAs) to cleave target RNAs. Unlike the DNA endonucleases Cas9 and Cpf1, which cleave only its DNA target, RNA-guided RNases, like C2c2, remains active after cleaving its RNA target, leading to "collateral" cleavage of non-targeted RNAs in proximity (Abudayyeh et al., 2016). This crRNA-programmed collateral RNA cleavage activity presents the opportunity to use RNA-guided RNases to detect the presence of a specific RNA by triggering in vivo programmed cell death or in vitro nonspecific RNA degradation that can serve as a readout (Abudayyeh et al., 2016; East-Seletsky et al., 2016).

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein His A, C or U. In certain embodiments, the effector protein may be *Leptotrichia shahii* C2c2p, more preferably *Leptotrichia shahii* DSM 19757 C2c2, and the 3' PAM is a 5' H.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

The nucleic acid molecule encoding a CRISPR effector protein, in particular C2c2, is advantageously a codon optimized CRISPR effector protein. An example of a codon optimized sequence, is in this instance a sequence optimized for expression in eukaryotes, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In one example embodiment, the effector protein comprises one or more HEPN domains comprising a RxxxxH motif sequence. The RxxxxH motif sequence can be, without limitation, from a HEPN domain described herein or a HEPN domain known in the art.

RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In particular embodiments, the Type VI RNA-targeting Cas enzyme is C2c2, or Cas13a. In other example embodiments, the Type VI RNA-targeting Cas enzyme is Cas13b. In particular embodiments, the homologue or orthologue of a Type VI protein such as C2c2 as referred to herein has a sequence homology or identity of at least 30%, or at least 40%, or at least 50%, or at least 60%, or at least 70%, or at least 80%, more preferably at least 85%, even more preferably at least 90%, such as for instance at least 95% with a Type VI protein such as C2c2 (e.g., based on the wild-type sequence of any of *Leptotrichia shahii* C2c2, *Lachnospiraceae bacterium* MA2020 C2c2, *Lachnospiraceae bacterium* NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, *Listeriaceae bacterium* (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2). In further embodiments, the homologue or orthologue of a Type VI protein such as C2c2 as referred to herein has a sequence identity of at least 30%, or at least 40%, or at least 50%, or at least 60%, or at least 70%, or at least 80%, more preferably at least 85%, even more preferably at least 90%, such as for instance at least 95% with the wild type C2c2 (e.g., based on the wild-type sequence of any of *Leptotrichia shahii* C2c2, *Lachnospiraceae bacterium* MA2020 C2c2, *Lachnospiraceae bacterium* NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, *Listeriaceae bacterium* (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2).

In certain other example embodiments, the CRISPR system the effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016 bearing Broad Institute No. 10035.PA4. Reference is further made to East-Seletsky et al. "Two distinct RNase activities of CRISPR-C2c2 enable guide-RNA processing and RNA detection" Nature doi: 10/1038/nature19802 and Abudayyeh et al. "C2c2 is a single-component programmable RNA-guided RNA targeting CRISPR effector" bioRxiv doi: 10.1101/054742.

In an embodiment, the Cas protein may be a C2c2 ortholog of an organism of a genus which includes but is not limited to *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter*, and *Lachnospira*. Species of organism of such a genus can be as otherwise herein discussed.

In certain example embodiments, the C2c2 effector proteins of the invention include, without limitation, the following 21 ortholog species including multiple CRISPR loci: *Leptotrichia shahii; Leptotrichia wadei* (Lw2); *Listeria seeligeri; Lachnospiraceae bacterium* MA2020; *Lachnospiraceae bacterium* NK4A179; [*Clostridium*] *aminophilum* DSM 10710; *Carnobacterium gallinarum* DSM 4847; *Carnobacterium gallinarum* DSM 4847 (second CRISPR Loci); *Paludibacter propionicigenes* WB4; *Listeria weihenstephanensis* FSL R9-0317; *Listeriaceae bacterium* FSL M6-0635; *Leptotrichia wadei* F0279; *Rhodobacter capsulatus* SB 1003; *Rhodobacter capsulatus* R121; *Rhodobacter capsulatus* DE442; *Leptotrichia buccalis* C-1013-b; *Herbinix hemicellulosilytica*; [*Eubacterium*] *rectale*; *Eubacteriaceae bacterium* CHKCI004; *Blautia* sp. Marseille-P2398; and *Leptotrichia* sp. oral taxon 879 str. F0557. Twelve (12) further non-limiting examples are: *Lachnospiraceae bacterium* NK4A144; *Chloroflexus aggregans; Demequina aurantiaca; Thalassospira* sp. TSL5-1; *Pseudobutyrivibrio* sp. OR37; *Butyrivibrio* sp. YAB3001; *Blautia* sp. Marseille-P2398; *Leptotrichia* sp. Marseille-P3007; *Bacteroides ihuae; Porphyromonadaceae bacterium* KH3CP3RA; *Listeria riparia*; and *Insolitispirillum peregrinum*.

In embodiments, the C2c2 protein as referred to herein also encompasses a functional variant of C2c2 or a homologue or an orthologue thereof. A "functional variant" of a protein as used herein refers to a variant of such protein which retains at least partially the activity of that protein. Functional variants may include mutants (which may be insertion, deletion, or replacement mutants), including polymorphs, etc. Also included within functional variants are fusion products of such protein with another, usually unrelated, nucleic acid, protein, polypeptide or peptide. Functional variants may be naturally occurring or may be man-made. Advantageous embodiments can involve engineered or non-naturally occurring Type VI RNA-targeting effector protein.

In an embodiment, nucleic acid molecule(s) encoding the C2c2 or an ortholog or homolog thereof, may be codon-optimized for expression in a eukaryotic cell. A eukaryote can be as herein discussed. Nucleic acid molecule(s) can be engineered or non-naturally occurring.

In an embodiment, the C2c2 or an ortholog or homolog thereof, may comprise one or more mutations and hence nucleic acid molecule(s) coding for same may have mutation(s). The mutations may be artificially introduced mutations and may include but are not limited to one or more mutations in a catalytic domain. Examples of catalytic domains with reference to a Cas9 enzyme may include but are not limited to RuvC I, RuvC II, RuvC III and HNH domains.

The CRISPR-SHERLOCK method may be a Cas13-based CRISPR-SHERLOCK method (see Gootenberg et al. Science 356 (6336): 438-442 (2017); Gootenberg et al. Science 360:439-444 (2018); Myhrvold et al. Science 360: 444-448 (2018); PCT/US17/65477).

In some embodiments, the amplified target nucleic acid may also be detected using a CRISPR Cas12-based detection system. The Cas12-based detection system may comprise a Cas12a, a Cas12b, or a Cas12c enzyme.

The Cas12-based detection system may comprise a Cas12 enzyme that is from an organism of a genus selected from the group consisting of *Francisella tularensis, Prevotella albensis, Lachnospiraceae bacterium, Butyrivibrio proteoclasticus, Peregrinibacteria bacterium, Parcubacteria bacterium, Smithella* sp., *Acidaminococcus* sp., *Lachnospiraceae* bacterium, *Candidatus Methanoplasma termitum, Eubacterium eligens, Moraxella* bovoculi, *Leptospira inadai, Porphyromonas* crevioricanis, *Prevotella disiens* and *Porphyromonas macacae, Succinivibrio dextrinosolvens, Prevotella disiens, Flavobacterium branchiophilum, Helcococcus kunzii, Eubacterium* sp., *Microgenomates* (Roizmanbacteria) bacterium, *Flavobacterium* sp., *Prevotella brevis, Moraxella caprae, Bacteroidetes oral, Porphyromonas cansulci, Synergistes jonesii, Prevotella bryantii, Anaerovibrio* sp., *Butyrivibrio fibrisolvens, Candidatus Methanomethylophilus, Butyrivibrio* sp., *Oribacterium* sp., *Pseudobutyrivibrio ruminis* and *Proteocatella sphenisci.*

Guide Sequences

As used herein, the term "guide sequence," "crRNA," "guide RNA," or "single guide RNA," or "gRNA" refers to a polynucleotide comprising any polynucleotide sequence having sufficient complementarity with a target nucleic acid sequence to hybridize with the target nucleic acid sequence and to direct sequence-specific binding of a RNA-targeting complex comprising the guide sequence and a CRISPR effector protein to the target nucleic acid sequence. In some example embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide may be selected to target any target nucleic acid sequence. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106 (1): 23-24; and PA Carr and GM Church, 2009, Nature Biotechnology 27 (12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In general, the CRISPR-Cas, CRISPR-Cas9 or CRISPR system may be as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, a CRISPR system comprises one or more nuclear exports signals (NESs). In some embodiments, a CRISPR system comprises one or more NLSs and one or more NESs. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments of CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

Guide Modifications

In certain embodiments, guides of the invention comprise non-naturally occurring nucleic acids and/or non-naturally occurring nucleotides and/or nucleotide analogs, and/or chemical modifications. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, boranophosphate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, 2-thiouridine analogs, N6-methyladenosine analogs, or 2'-fluoro analogs. Further examples of modified bases include, but are not limited to, 2-aminopurine, 5-bromo-uridine, pseudouridine ($\Psi$), N1-methylpseudouridine (me$^1\Psi$), 5-methoxyuridine (5moU), inosine, 7-methylguanosine. Examples of guide RNA chemical modifications include, without limitation, incorporation of 2'-O-methyl (M), 2'-O-methyl-3'-phosphorothioate (MS), phosphorothioate (PS), S-constrained ethyl (cEt), or 2'-O-methyl-3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33 (9): 985-9, doi: 10.1038/nbt.3290, published online 29 Jun. 2015; Ragdarm et al., 0215, *PNAS*, E7110-E7111; Allerson et al., *J. Med. Chem.* 2005, 48:901-904; Bramsen et al., *Front. Genet.,* 2012, 3:154; Deng et al., *PNAS,* 2015, 112:11870-11875; Sharma et al., *MedChemComm.,* 2014, 5:1454-1471; Hendel et al., *Nat. Biotechnol.* (2015) 33 (9): 985-989; Li et al., *Nature Biomedical Engineering,* 2017, 1, 0066 DOI: 10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target DNA and one or more deoxyribonucleotides and/or nucleotide analogs in a region that binds to Cas9, Cpf1, or C2c1. In an embodiment of the invention, deoxyribonucleotides and/or nucleotide analogs are incorporated in engineered guide structures, such as, without limitation, 5' and/or 3' end, stem-loop regions, and the seed region. In certain embodiments, the modification is not in the 5'-handle of the stem-loop regions. Chemical modification in the 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl-3'-phosphorothioate (MS), S-constrained ethyl (cEt), or 2'-O-methyl-3'-thioPACE (MSP). Such modification can enhance genome editing efficiency (see Hendel et al., *Nat. Biotechnol.* (2015) 33 (9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl (cEt). Such chemically modified guide can mediate enhanced levels of gene disruption (see Ragdarm et al., 0215, *PNAS*, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6: e25312, DOI: 10.7554).

In certain embodiments, the CRISPR system as provided herein can make use of a crRNA or analogous polynucleotide comprising a guide sequence, wherein the polynucleotide is an RNA, a DNA or a mixture of RNA and DNA, and/or wherein the polynucleotide comprises one or more nucleotide analogs. The sequence can comprise any structure, including but not limited to a structure of a native crRNA, such as a bulge, a hairpin or a stem loop structure. In certain embodiments, the polynucleotide comprising the guide sequence forms a duplex with a second polynucleotide sequence which can be an RNA or a DNA sequence.

In certain embodiments, use is made of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33 (9): 985-9, doi: 10.1038/nbt.3290, published online 29 Jun. 2015). Chemically modified guide RNAs further include, without limitation, RNAs with phosphorothioate linkages and locked nucleic acid (LNA) nucleotides comprising a methylene bridge between the 2' and 4' carbons of the ribose ring.

In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 to 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay. Similarly, cleavage of a target RNA may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine (Y), N1-methylpseudouridine (me$^1$Ψ), 5-methoxyuridine (5moU), inosine, 7-methyl-guanosine, 2'-O-methyl-3'-phosphorothioate (MS), S-constrained ethyl (cEt), phosphorothioate (PS), or 2'-O-methyl-3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 or 10 nucleotides in the 3'-terminus are chemically modified. Such chemical modifications at the 3'-terminus of the Cpf1 CrRNA improve gene cutting efficiency (see Li, et al., *Nature Biomedical Engineering*, 2017, 1:0066). In a specific embodiment, 5 nucleotides in the 3'-terminus are replaced with 2'-fluoro analogues. In a specific embodiment, 10 nucleotides in the 3'-terminus are replaced with 2'-fluoro analogues. In a specific embodiment, 5 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the loop comprises 3, 4, or 5 nucleotides. In certain embodiments, the loop comprises the sequence of UCUU, UUUU, UAUU, or UGUU.

A guide sequence, and hence a nucleic acid-targeting guide RNA may be selected to target any target nucleic acid sequence. In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target RNA may be an RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell. The target sequence may be DNA. The target sequence may be any RNA sequence. In some embodiments, the target sequence may be a sequence within a RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nuclear RNA (snoRNA), double stranded RNA (dsRNA), non-coding RNA (ncRNA), long non-coding RNA (lncRNA), and small cytoplasmic RNA (scRNA). In some preferred embodiments, the target sequence may be a sequence within a RNA molecule selected from the group consisting of mRNA, pre-mRNA, and rRNA. In some preferred embodiments, the target sequence may be a sequence within a RNA molecule selected from the group consisting of ncRNA, and lncRNA. In some more preferred embodiments, the target sequence may be a sequence within an mRNA molecule or a pre-mRNA molecule.

In certain embodiments, the spacer length of the guide RNA is less than 28 nucleotides. In certain embodiments, the spacer length of the guide RNA is at least 18 nucleotides and less than 28 nucleotides. In certain embodiments, the spacer length of the guide RNA is between 19 and 28 nucleotides. In certain embodiments, the spacer length of the guide RNA is between 19 and 25 nucleotides. In certain embodiments, the spacer length of the guide RNA is 20 nucleotides. In certain embodiments, the spacer length of the guide RNA is 23 nucleotides. In certain embodiments, the spacer length of the guide RNA is 25 nucleotides.

In certain embodiments, modulations of cleavage efficiency can be exploited by introduction of mismatches, e.g. 1 or more mismatches, such as 1 or 2 mismatches between spacer sequence and target sequence, including the position of the mismatch along the spacer/target. The more central (i.e. not 3' or 5') for instance a double mismatch is, the more cleavage efficiency is affected. Accordingly, by choosing mismatch position along the spacer, cleavage efficiency can be modulated. By means of example, if less than 100% cleavage of targets is desired (e.g. in a cell population), 1 or more, such as preferably 2 mismatches between spacer and target sequence may be introduced in the spacer sequences. The more central along the spacer of the mismatch position, the lower the cleavage percentage.

In certain example embodiments, the cleavage efficiency may be exploited to design single guides that can distinguish two or more targets that vary by a single nucleotide, such as a single nucleotide polymorphism (SNP), variation, or (point) mutation. The CRISPR effector may have reduced sensitivity to SNPs (or other single nucleotide variations) and continue to cleave SNP targets with a certain level of efficiency. Thus, for two targets, or a set of targets, a guide RNA may be designed with a nucleotide sequence that is complementary to one of the targets i.e. the on-target SNP. The guide RNA is further designed to have a synthetic mismatch. As used herein a "synthetic mismatch" refers to a non-naturally occurring mismatch that is introduced upstream or downstream of the naturally occurring SNP, such as at most 5 nucleotides upstream or downstream, for instance 4, 3, 2, or 1 nucleotide upstream or downstream, preferably at most 3 nucleotides upstream or downstream, more preferably at most 2 nucleotides upstream or downstream, most preferably 1 nucleotide upstream or downstream (i.e. adjacent the SNP). When the CRISPR effector binds to the on-target SNP, only a single mismatch will be formed with the synthetic mismatch and the CRISPR effector will continue to be activated and a detectable signal produced. When the guide RNA hybridizes to an off-target SNP, two mismatches will be formed, the mismatch from the SNP and the synthetic mismatch, and no detectable signal generated. Thus, the systems disclosed herein may be designed to distinguish SNPs within a population. For, example the systems may be used to distinguish pathogenic strains that differ by a single SNP or detect certain disease specific SNPs, such as but not limited to, disease associated SNPs, such as without limitation cancer associated SNPs.

In certain embodiments, the guide RNA is designed such that the SNP is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the SNP is located on position 1, 2, 3, 4, 5, 6, 7, 8, or 9 of the spacer sequence (starting at the 5' end). In certain embodiments, the guide RNA is designed such that the SNP is located on position 2, 3, 4, 5, 6, or 7 of the spacer sequence (starting at the 5' end). In certain embodiments, the guide RNA is designed such that the SNP is located on position 3, 4, 5, or 6 of the spacer sequence (starting at the 5' end). In certain embodiments, the guide RNA is designed such that the SNP is located on position 3 of the spacer sequence (starting at the 5' end).

In certain embodiments, the guide RNA is designed such that the mismatch (e.g. the synthetic mismatch, i.e. an additional mutation besides a SNP) is located on position 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the spacer sequence (starting at the 5' end). In certain embodiments, the guide RNA is designed such that the mismatch is located on position 1, 2, 3, 4, 5, 6, 7, 8, or 9 of the spacer sequence (starting at the 5' end). In certain embodiments, the guide RNA is designed such that the mismatch is located on position 4, 5, 6, or 7 of the spacer sequence (starting at the 5' end. In certain embodiments, the guide RNA is designed such that the mismatch is located on position 5 of the spacer sequence (starting at the 5' end).

In certain embodiments, the guide RNA is designed such that the mismatch is located 2 nucleotides upstream of the SNP (i.e. one intervening nucleotide).

In certain embodiments, the guide RNA is designed such that the mismatch is located 2 nucleotides downstream of the SNP (i.e. one intervening nucleotide).

In certain embodiments, the guide RNA is designed such that the mismatch is located on position 5 of the spacer sequence (starting at the 5' end) and the SNP is located on position 3 of the spacer sequence (starting at the 5' end).

The embodiments described herein comprehend inducing one or more nucleotide modifications in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s). The mutations can include the introduction, deletion, or substitution of 1-75 nucleotides at each target sequence of said cell(s) via the guide(s) RNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s). The mutations can include the introduction, deletion, or substitution of 40, 45, 50, 75, 100, 200, 300, 400 or 500 nucleotides at each target sequence of said cell(s) via the guide(s) RNA(s).

Typically, in the context of an endogenous CRISPR system, formation of a CRISPR complex (comprising a guide sequence hybridized to a target sequence and complexed with one or more Cas proteins) results in cleavage in or near (e.g. within 1, 2, 3, 4, 5, 6, 7, 8, 9, 10, 20, 50, or more base pairs from) the target sequence, but may depend on for instance secondary structure, in particular in the case of RNA targets.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105, 031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256, 912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. applications 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. applications 62/098,059, 30 Dec. 2014, 62/181,641, 18 Jun. 2015, and 62/181,667, 18 Jun. 2015, RNA-TARGETING SYSTEM; U.S. applications 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; US application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. applications 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. applications 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Systems for Detecting Target Nucleic Acid Sequences

In certain example embodiments, the invention provides a system for detecting a target nucleic acid sequence in a sample. The system may comprise a transposon complex as described herein. The transposon complex may comprise a transposase and a transposon sequence comprising one or more T7 RNA polymerase promoters as described herein. The transposase may insert one or more T7 RNA polymerase promoters into an oligonucleotide comprising the target nucleic acid sequence.

In some embodiments, the system may further comprise a T7 RNA polymerase.

The T7 RNA polymerase may transcribe the target nucleic acid from one of the inserted T7 promoters as described herein.

The system may further comprise a CRISPR-based detection system for detecting the transcribed target nucleic acid as described herein. In some embodiments, the CRISPR-based detection system may be a CRISPR-Cas13-based detection system. The CRISPR Cas13-based detection system may be a CRISPR-SHERLOCK detection system. In some embodiments, the CRISPR-based detection system may be a CRISPR-Cas12-based detection system, as described herein.

In certain example embodiments, the transposase may be a Tn5 transposase or variant thereof. The transposase may be an engineered transposase as described herein. In certain example embodiments, the transposon sequence may comprise two 19 base pair ME Tn5 transposase recognition sequences, as described herein.

In certain example embodiments, the CRISPR-SHER-LOCK system may be a Cas13-based CRISPR-SHERLOCK system as described herein.

In certain example embodiments, the system for detecting a target nucleic acid sequence may further comprise reagents for nucleic acid amplification as described herein.

In certain example embodiments, the system for detecting a target nucleic acid sequence may further comprise reagents for reverse transcribing a target sequence comprising RNA.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of detecting a target nucleic acid sequence, comprising:
(a) contacting an oligonucleotide comprising the target nucleic acid sequence with a transposon complex, wherein the transposon complex comprises a transposase and a transposon sequence comprising one or more T7 RNA polymerase promoters;
(b) inserting the one or more T7 RNA polymerase promoters into the oligonucleotide using the transposase;
(c) amplifying the target nucleic acid sequence by generating RNA oligonucleotides comprising the target nucleic acid sequence via transcription from the inserted one or more T7 RNA polymerase promoters, and
(d) detecting the target nucleic acid sequence using a CRISPR-Cas detection system,
wherein the CRISPR-Cas detection system comprises a CRISPR effector protein and a guide sequence that is complementary to the target nucleic acid sequence.

2. The method of claim 1, wherein the CRISPR-Cas detection system is a CRISPR-Cas13 detection system.

3. The method of claim 1, wherein the transposase is a Tn5 transposase, a Mu transposase, or a Tn7 transposase.

4. The method of claim 3, wherein the transposase is a Tn5 transposase.

5. The method of claim 4, wherein the transposon sequence comprises two 19 base pair Mosaic End (ME) Tn5 transposase recognition sequences.

6. The method of claim 1, wherein the transposase is an engineered transposase.

7. The method of claim 6, wherein the engineered transposase is optimized to function between 30 and 45 degrees C., more preferably between 35 and 40 degrees C.

8. The method of claim 6, wherein the engineered transposase is optimized to release from the oligonucleotide at a faster rate compared to a wild-type transposase.

9. The method of claim 1, wherein insertion of the one or more T7 RNA polymerase promoters into the oligonucleotide is random.

10. The method of claim 1, wherein the oligonucleotide is double-stranded.

11. The method of claim 10, wherein insertion of the one or more T7 RNA polymerase promoters into the double-stranded oligonucleotide occurs in a GC rich region of the double-stranded oligonucleotide.

12. The method of claim 2, wherein the CRISPR-Cas detection system comprises a Cas13 enzyme that is from an organism of a genus selected from the group consisting of: *Leptotrichia, Listeria, Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter,* and *Lachnospira.*

13. The method of claim 12, wherein the Cas13 enzyme is from an organism selected from the group consisting of: *Leptotrichia shahii; Leptotrichia wadei* (Lw2); *Listeria seeligeri; Lachnospiraceae bacterium* MA2020; *Lachnospiraceae bacterium* NK4A179; *[Clostridium] aminophilum* DSM 10710; *Carnobacterium gallinarum* DSM 4847; *Carnobacterium gallinarum* DSM 4847 (second CRISPR Loci); *Paludibacter propionicigenes* WB4; *Listeria weihenstephanensis* FSL R9-0317; *Listeriaceae bacterium* FSL M6-0635; *Leptotrichia wadei* F0279; *Rhodobacter capsulatus* SB 1003; *Rhodobacter capsulatus* R121; *Rhodobacter capsulatus* DE442; *Leptotrichia buccalis* C-1013-b; *Herbinix hemicellulosilytica; [Eubacterium] rectale; Eubacteriaceae bacterium* CHKCI004; *Blautia* sp. Marseille-P2398; *Leptotrichia* sp. oral taxon 879 str. F0557; *Lachnospiraceae bacterium* NK4A144; *Chloroflexus aggregans; Demequina aurantiaca; Thalassospira* sp. TSL5-1; *Pseudobutyrivibrio* sp. OR37; *Butyrivibrio* sp. YAB3001; *Blautia* sp. Marseille-P2398; *Leptotrichia* sp. Marseille-P3007; *Bacteroides ihuae; Porphyromonadaceae bacterium* KH3CP3RA; *Listeria riparia;* and *Insolitispirillum peregrinum.*

14. The method of claim 1, wherein the CRISPR-Cas detection system is a CRISPR-Cas12 detection system.

15. The method of claim 14, wherein the CRISPR-Cas12 detection system comprises a Cas12a or Cas12b enzyme.

16. The method of claim 14, wherein the CRISPR-Cas12 detection system comprises a Cas12 enzyme that is from an organism of a genus selected from the group consisting of *Francisella tularensis, Prevotella albensis, Lachnospiraceae bacterium, Butyrivibrio proteoclasticus, Peregrinibacteria bacterium, Parcubacteria bacterium, Smithella* sp., *Acidaminococcus* sp., *Lachnospiraceae bacterium, Candidatus Methanoplasma termitum, Eubacterium eligens, Moraxella bovoculi, Leptospira inadai, Porphyromonas crevioricanis, Prevotella disiens* and *Porphyromonas macacae, Succinivibrio dextrinosolvens, Prevotella disiens, Flavobacterium branchiophilum, Helcococcus kunzii, Eubacterium* sp., *Microgenomates (Roizmanbacteria) bacterium, Flavobacterium* sp., *Prevotella brevis, Moraxella caprae, Bacteroidetes oral, Porphyromonas cansulci, Synergistes jonesii, Prevotella bryantii, Anaerovibrio* sp., *Butyrivibrio fibrisolvens, Candidatus Methanomethylophilus, Butyrivibrio* sp., *Oribacterium* sp., *Pseudobutyrivibrio ruminis* and *Proteocatella sphenisci.*

17. The method of claim 1, wherein the method does not require heating the oligonucleotide.

18. The method of claim 17, wherein amplification of the target nucleic acid sequence is performed at a constant temperature.

19. The method of claim 1, wherein the target nucleic acid sequence is about 20-30, about 30-40, about 40-50, or about 50-100 nucleotides in length, wherein the target nucleic acid sequence is about 100-200, about 100-500, or about 100-1000 nucleotides in length, or wherein the target nucleic acid sequence is about 1000-2000, about 2000-3000, about 3000-4000, or about 4000-5000 nucleotides in length.

20. The method of claim 1, further comprising detecting the amplified nucleic acid by a method selected from the group consisting of gel electrophoresis, intercalating dye detection, fluorescence, Fluorescence Resonance Energy Transfer (FRET), mass spectrometry, real-time RPA, real-time LAMP, real-time NEAR, real-time HDA, real-time TMA, real-time NASBA, and CRISPR-SHERLOCK.

21. The method of claim 1, wherein the target nucleic acid is detected at femtomolar sensitivity or at attomolar sensitivity.

22. The method of claim 1, wherein the oligonucleotide comprising the target nucleic acid is selected from the group consisting of genomic DNA, mitochondrial DNA, viral DNA, plasmid DNA, and synthetic double-stranded DNA.

23. The method of claim 1, wherein the oligonucleotide comprising the target nucleic acid is an RNA oligonucleotide, and wherein the method comprises a reverse transcription step prior to contacting the oligonucleotide with the transposon complex.

24. The method of claim 1, wherein the target nucleic acid sequence comes from a sample, and wherein the sample is a biological sample or an environmental sample.

25. The method of claim 24, wherein the biological sample is a blood, plasma, serum, urine, stool, sputum, mucous, lymph fluid, synovial fluid, bile, ascites, pleural effusion, seroma, saliva, cerebrospinal fluid, aqueous or vitreous humor sample, or any bodily secretion, a transudate, an exudate, or fluid obtained from a joint, or a swab of skin or mucosal membrane surface.

26. The method of claim 25, wherein the sample is blood, plasma or serum obtained from a human patient.

27. The method of claim 24, wherein the sample is a plant sample.

28. The method of claim 24, wherein the sample is a crude sample or a purified sample.

29. A system for detecting a target nucleic acid sequence in a sample, the system comprising:

a transposon complex, wherein the transposon complex comprises a transposase and a transposon sequence comprising one or more T7 RNA polymerase promoters, wherein the transposase randomly inserts the one or more T7 RNA polymerase promoters into an oligonucleotide comprising the target nucleic acid sequence;

a T7 RNA polymerase, wherein the T7 RNA polymerase transcribes the target nucleic acid sequence from the randomly inserted one or more T7 promoters; and a CRISPR-Cas detection system for detecting the target nucleic acid sequence transcribed by the T7 RNA polymerase, wherein the CRISPR-Cas detection system comprises a CRISPR effector protein and a guide sequence that is complementary to the target nucleic acid sequence.

30. The system of claim 29, wherein the CRISPR-Cas detection system is a CRISPR-Cas13-SHERLOCK system.

31. The system of claim 29, wherein the transposase is a Tn5 transposase or a variant thereof.

32. The system of claim 29, wherein the transposon sequence comprises two 19 base pair ME Tn5 transposase recognition sequences.

33. The system of claim 29, wherein the CRISPR-Cas detection system is a CRISPR-Cas12 detection system.

34. The system of claim 29, further comprising reagents for isothermal recombinase polymerase amplification (RPA).

35. The system of claim 29, further comprising reverse transcription reagents.

\* \* \* \* \*